(12) United States Patent
Nakagami et al.

(10) Patent No.: US 9,101,749 B2
(45) Date of Patent: Aug. 11, 2015

(54) INDWELLING CATHETER

(71) Applicant: NIPRO CORPORATION, Osaka-shi, Osaka (JP)

(72) Inventors: Hiroyuki Nakagami, Osaka (JP); Tatsuya Kudo, Osaka (JP); Tomohiro Uchimura, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days.

(21) Appl. No.: 14/348,486

(22) PCT Filed: Oct. 2, 2012

(86) PCT No.: PCT/JP2012/006318
§ 371 (c)(1),
(2) Date: Mar. 28, 2014

(87) PCT Pub. No.: WO2013/051242
PCT Pub. Date: Apr. 11, 2013

(65) Prior Publication Data
US 2014/0236099 A1    Aug. 21, 2014

(30) Foreign Application Priority Data

Oct. 5, 2011  (JP) .................................. 2011-220629

(51) Int. Cl.
*A61M 5/178* (2006.01)
*A61M 39/06* (2006.01)
*A61M 25/00* (2006.01)

(52) U.S. Cl.
CPC ....... *A61M 39/0613* (2013.01); *A61M 25/0017* (2013.01); *A61M 25/0097* (2013.01); *A61M 39/06* (2013.01); *A61M 2039/062* (2013.01); *A61M 2039/064* (2013.01)

(58) Field of Classification Search
CPC ............ A61M 39/26; A61M 25/0097; A61M 25/0017; A61M 2039/1077; A61M 25/0014; A61M 2039/062; A61M 39/0613; A61M 2039/0633; A61M 25/0075; A61M 39/06; A61M 2039/064; A61B 5/150221; A61B 5/150488; A61B 5/150496; A61B 5/15011; A61B 5/150519; Y10S 128/912
USPC ...................................... 604/167.01
See application file for complete search history.

(56) References Cited

U.S. PATENT DOCUMENTS

| | | | |
|---|---|---|---|
| 5,458,640 | A | 10/1995 | Gerrone |
| 5,613,663 | A | 3/1997 | Schmidt et al. |

(Continued)

FOREIGN PATENT DOCUMENTS

| | | |
|---|---|---|
| JP | A-08-219314 | 8/1996 |
| JP | A-2008-173206 | 7/2008 |

(Continued)

OTHER PUBLICATIONS

International Preliminary Report on Patentability issued in International Application No. PCT/JP2012/006318 on Apr. 8, 2014 (with translation).

(Continued)

*Primary Examiner* — Jason Flick
(74) *Attorney, Agent, or Firm* — Oliff PLC (57) ABSTRACT

An indwelling catheter including: a hollow catheter base having a tip and a back end, the back end being able to receive and connect a male connector; a tube provided at the tip of the catheter base; a flexible hemostasis valve installed inside the catheter base; a pusher installed at a back of the hemostasis valve; and a pusher guide installed between the pusher and the catheter base. The pusher has a hollow constitution whose taper reduces in diameter facing its tip. The pusher guide is able to restrict a position of the pusher at a first position where the pusher does not push open the hemostasis valve and a second position where the taper of the pusher is positioned inside the hemostasis valve and pushes open the hemostasis valve.

4 Claims, 6 Drawing Sheets

(56) References Cited

U.S. PATENT DOCUMENTS

| | | | |
|---|---|---|---|
| 7,682,340 B2 * | 3/2010 | Funamura et al. | 604/167.03 |
| 2004/0210194 A1 | 10/2004 | Bonnette et al. | |
| 2008/0208132 A1 | 8/2008 | Funamura et al. | |
| 2010/0204648 A1 | 8/2010 | Stout et al. | |
| 2010/0204660 A1 | 8/2010 | Mckinnon et al. | |

FOREIGN PATENT DOCUMENTS

| | | |
|---|---|---|
| JP | A-2011-115630 | 6/2011 |
| WO | 03/002182 A1 | 1/2003 |

OTHER PUBLICATIONS

International Search Report issued in International Application No. PCT/JP2012/006318 dated Dec. 18, 2012 (with translation).

May 22, 2015 Extended European Search Report issued in European Application No. 12838983.0.

\* cited by examiner

INDWELLING CATHETER

TECHNICAL FIELD

The present invention relates to an improvement in the connector part of an indwelling catheter that is indwelling in an artery, a vein or the like, used for transfusions, blood transfusions, artificial dialysis or the like, and particularly to an indwelling catheter that improves connecting operability while preventing blood leakage from the catheter until a transfusion line is connected to the catheter when the catheter is indwelling in the artery, vein or the like.

BACKGROUND ART

As an indwelling catheter, the item disclosed in FIGS. 1 to 4 of Japanese Unexamined Patent Publication No. JP-A-2011-115630 (Patent Document 1) is well known as a prior example. This conventional indwelling catheter is equipped with a hollow catheter base, a catheter tube, a flexible hemostasis valve, and a hollow pusher installed to be able to slide inside the catheter base for doing the opening and closing operation of the hemostasis valve, and the hemostasis valve is constituted having a pusher receiving part that encloses and holds the outer circumference of the pusher.

Then, for the operation, by the hemostasis valve having a pusher receiving part that encloses and holds the outer circumference of the pusher, during puncturing (before removal of the inner needle), the inner needle passes through the pusher and the hemostasis valve and is made to face the needle tip from the tip of the catheter tube (state for which puncture is possible), and after puncturing (when the inner needle is removed), the hemostasis valve is resealed (valve closed) so that blood leakage is prevented (hemostatic condition), and also, by connecting a male connector from the back of the catheter base, the pusher passes through the hemostasis valve and is locked at the front position, and the pusher stops at the same position, so even if the male connector is removed, the hemostasis function is not expressed, and a conductive state between the catheter base and the catheter tube is maintained.

However, with the indwelling catheter noted above, when the patient temporarily suspends treatment, and it is necessary to remove the male connector (e.g. when treatment is temporarily suspended due to a physiological phenomenon such as the patient experiencing an urge to urinate or the like), there is the disadvantage of having to temporarily block the catheter using some kind of method.

To eliminate the problem described above, as an indwelling catheter that can be connected a plurality of times, the item disclosed in Japanese Unexamined Patent Publication No. JP-A-2008-173206 (Patent Document 2) is well known as a prior example.

This indwelling catheter is linked to the base of a cannula, and has an outer needle main unit with an empty space part in communication with the inner cavity of the cannula provided on the interior. On the interior of this outer needle main unit, a connector part is provided in a movable state, and a valve body is installed in front of the connector part. This valve body passes through the tip side part of the connector part in liquid tight fashion, making the cannula inner cavity and the connector part flow path be in communication, and is also equipped with an opening and closing hole that is closed when the tip side part of the connector part is not inserted, and blocks the front part side and the back part side of the space part of the outer needle main unit. Furthermore, with this constitution, a valve body presser plate equipped with an insertion hole in which the tip side part of the connector part can be inserted is provided on the back surface side of the valve body, and a coil spring is installed between the valve body presser plate and a spring bearing part formed on the connector part.

Then, for the operation, when treatment is suspended and the male connector connection is temporarily canceled, the connector part is moved to the back by the coil spring provided inside the outer needle (catheter base), the valve body is closed, and blood leakage is prevented.

However, when using a constitution with a coil spring installed inside the catheter base, it is necessary to make the strength of the spring a fixed strength or greater to return the pusher reliably to its original position, and it is necessary that the coil spring have a certain degree of length. As a result, it is necessary to have a catheter base equipped with enough space to provide a coil spring of a sufficient length, and the size of the indwelling catheter becomes large, and a circumstance occurs for which it is difficult to fix to the skin, or for which the indwelling catheter gets in the way during treatment.

BACKGROUND ART DOCUMENTS

Patent Documents

Patent Document 1: JP-A-2011-115630
Patent Document 2: JP-A-2008-173206

SUMMARY OF THE INVENTION

Problem the Invention Attempts to Solve

The present invention was created to address the problems noted above, and an object is to provide an indwelling catheter that can be connected a plurality of times without needing to make the size larger, and that is an indwelling catheter with excellent operability.

Means for Solving the Problem

In light of this, as a result of earnest investigation by the inventors, the following invention was devised. The present invention provides an indwelling catheter including: a hollow catheter base having a tip and a back end, the back end being able to receive and connect a male connector configured to be inserted from a back end side exterior; a tube provided at the tip of the catheter base; a flexible hemostasis valve installed inside the catheter base; a pusher installed at a back of the hemostasis valve; and a pusher guide installed between the pusher and an inner wall of the catheter base, wherein the pusher has a hollow constitution, and has a taper that reduces in diameter facing a tip of the pusher, and the pusher guide has a constitution which is able to restrict a position of the pusher with the pusher at a first position for which the pusher does not push open the hemostasis valve, and a second position for which the taper of the pusher is positioned inside the hemostasis valve and does push open the hemostasis valve.

Also, the hemostasis valve can also be compressed by the catheter base. For example, preferably this hemostasis valve is pressed at the inner circumference surface of the catheter base at its outer circumference surface, and that compression force is applied in the catheter base axial perpendicular direction.

Also, it is also acceptable that the pusher guide forms a tube shape, a projecting part projecting inward in a radial direction is provided on an inner wall of the pusher guide, and movement of the pusher backward at the first position is restricted by the projecting part.

With this kind of indwelling catheter, first, from after inner needle removal until connection of the male connector, the circumstance of blood leaking to the outside is prevented by the hemostasis valve. Also, after connection of the male connector, when the necessity arises to temporarily release the connection of the male connector, simply by releasing the connection of the male connector, by the elastic force of the hemostasis valve applied to the taper at the tip part of the pusher positioned inside the opening and closing part of the hemostasis valve, the pusher is naturally moved to the back, and the hemostasis valve is closed. In this way, even when a complex structure such as a spring or the like is not provided inside the catheter base, it is possible to move the pusher to a position that does not push open the hemostasis valve, so an indwelling catheter is realized for which the catheter base size is small, and fixing the indwelling catheter to the skin of the patient is easy. Also, by having a pusher guide that restricts the movement of the pusher at the first position at which the hemostasis valve is not pushed open, and a second position at which the hemostasis valve is pushed open, there is no occurrence of the pusher exceeding a fixed position and separating from the hemostasis valve, and the circumstance does not occur of the pusher breaking away from the catheter base. Furthermore, wobbling of the pusher is prevented by the pusher guide, so even if connection and release of the male connector is performed a plurality of times, opening and closing of the hemostasis valve is performed precisely by the pusher, so it is possible to have an indwelling catheter that can be used with a sense of security by the user.

Also, by the hemostasis valve being compressed by the catheter base, it is possible to increase the elastic force inward in the radial direction of the hemostasis valve applied to the taper surface of the pusher tip part when the pusher is positioned at the second position.

Also, by the projecting part that projects inward in the radial direction being provided on the inner wall of the pusher guide, it is possible to suitably prevent the pusher in the first position from moving to the back.

EFFECT OF THE INVENTION

According to the present invention, it is possible to successfully prevent leakage of blood from the catheter from indwelling of the indwelling catheter to the skin to connection of the transfusion line, and from release of the transfusion line connection until reconnection without the user making a great effort, and it is possible to realize an indwelling catheter with excellent operability.

EMBODIMENTS FOR CARRYING OUT THE INVENTION

Following, we will describe the invention of this application using the drawings, but the invention of this application is not limited to the embodiments noted in these drawings. Also, for convenience, hereafter, we will describe the tip side of the indwelling catheter as the front, and the back end side of the indwelling catheter as the back.

FIG. 1 to FIG. 4 show an embodiment of an indwelling catheter of the present invention, and as shown in the drawings, the indwelling catheter 10 has a tube 12 provided at the tip side of the indwelling catheter 10, a catheter base 14 provided at the back of the tube 12, a hemostasis valve 16 provided inside the catheter base 14, a pusher 18, a pusher guide 20 and the like. With the description below, the first position is when the pusher 18 is, inside the catheter base 14, in a position which does not push open a slit 22 of the hemostasis valve 16, and the second position is when the pusher 18 is in a position that does push open the slit 22 of the hemostasis valve 16.

Figure 1:
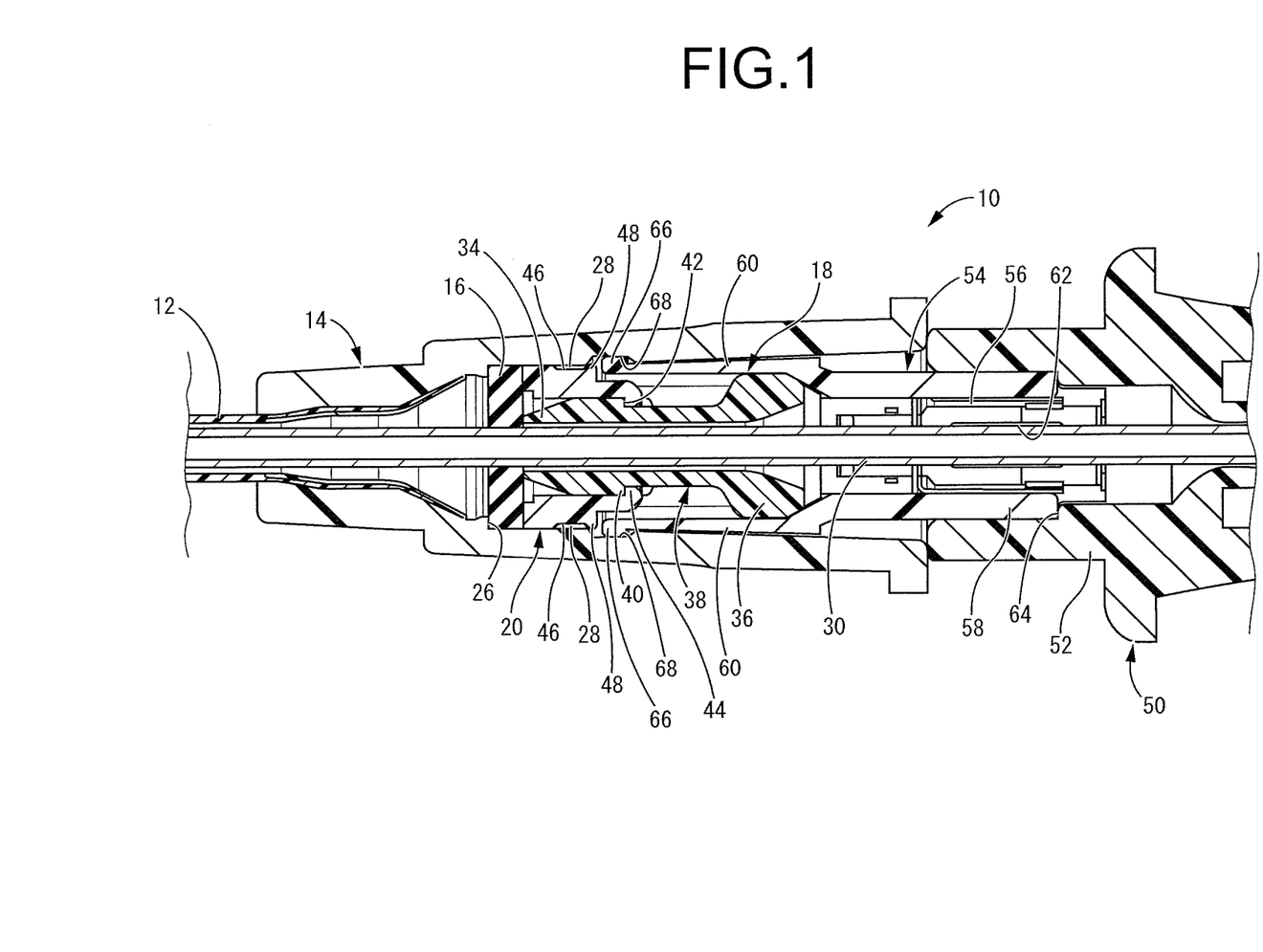
FIG. 1 is a cross sectional view showing the time of a skin puncture by an inner needle of an indwelling catheter of an embodiment of the indwelling catheter according to the present invention.

The tube 12 of this embodiment is a small diameter long tube, and is installed extending in the front-back direction (left-right direction in FIG. 1). This tube 12 is transparent or translucent, and is flexible. Also, the tube 12 is an integrally molded component made from a plastic (resin) material, and as this plastic material, for example, a thermoplastic resin can be used. As this thermoplastic resin, preferable examples include ethylene tetrafluoroethylene copolymer (ETFE), tetrafluoroethylene-perfluoroalkyl ether copolymer (PFA), polypropylene resin, polyethylene resin, polyurethane resin, polyamide resin and the like.

The catheter base 14 has a tip and a back end, and from the back end side exterior a syringe 24 as a male connector is configured to be releasably inserted and connected in a communication state. The catheter base 14 has a hollow, roughly tube shape whose tip and back end both open. Besides, with this embodiment, the back part of the tube 12 is fit onto the tip of the catheter base 14 in a communication state, and is fixed using an adhesive. Furthermore, a step 26 in contact with the front surface part of the hemostasis valve 16 installed inside the catheter base 14 is formed along the entire circumference on the inner circumference surface of the catheter base 14, and the outer circumference part of the hemostasis valve 16 is fixed by sandwiching in the axial direction by the step 26 and by the pusher guide 20 behind that. Also, the diameter of the inner circumference of the catheter base 14 abutting the hemostasis valve 16 is constituted to be smaller than the outer diameter of a free stand-alone unit of the hemostasis valve 16 before attachment, and in a state with the hemostasis valve 16 attached inside the catheter base 14, the hemostasis valve 16 is compressed inward in the radial direction. A pusher guide fixing part 28 that engages and fixes the pusher guide 20 is formed on the inner circumference surface of the catheter base 14 abutting the pusher guide 20 on one part of the circumference, and aligns and fixes the pusher guide 20 in the axial direction.

In FIG. 1 to FIG. 4 which show this embodiment, the pusher guide fixing part 28 is a projecting part that projects inward in the radial direction, but there is no limit on this as long as it is an item that can be engaged and fixed with the pusher guide 20. When doing a procedure, the catheter base 14 is preferably formed using a transparent or translucent material so as to be able to see through the inside of the catheter base 14, and is more preferably formed using a plastic (resin) material. As this plastic material, the same items as those for the tube 12 can be listed, for example.

The hemostasis valve 16 is a flexible valve structure, provided inside the catheter base 14 so that the front surface part is in contact with the back surface part of the step 26 inside the catheter base 14, and the outer circumference part thereof is fixed so as not to be moved in the forward direction when pushed to the front by the pusher 18. Also, the slit 22 that passes through in the front-back direction is formed on the center part of the hemostasis valve 16 of this embodiment. In FIG. 1, an inner needle 30 is inserted in the interior of the tube 12 and the catheter base 14, and passes through the hemostasis valve 16 so as to push open the slit 22. By the inner needle 30 being inserted in the slit 22, except for the outer circumference part that is sandwiched and fixed, the hemostasis valve 16 is slightly deformed by bulging or tilting or the like in the axial direction, but an illustration of the deformed state has been omitted.

Figure 3:
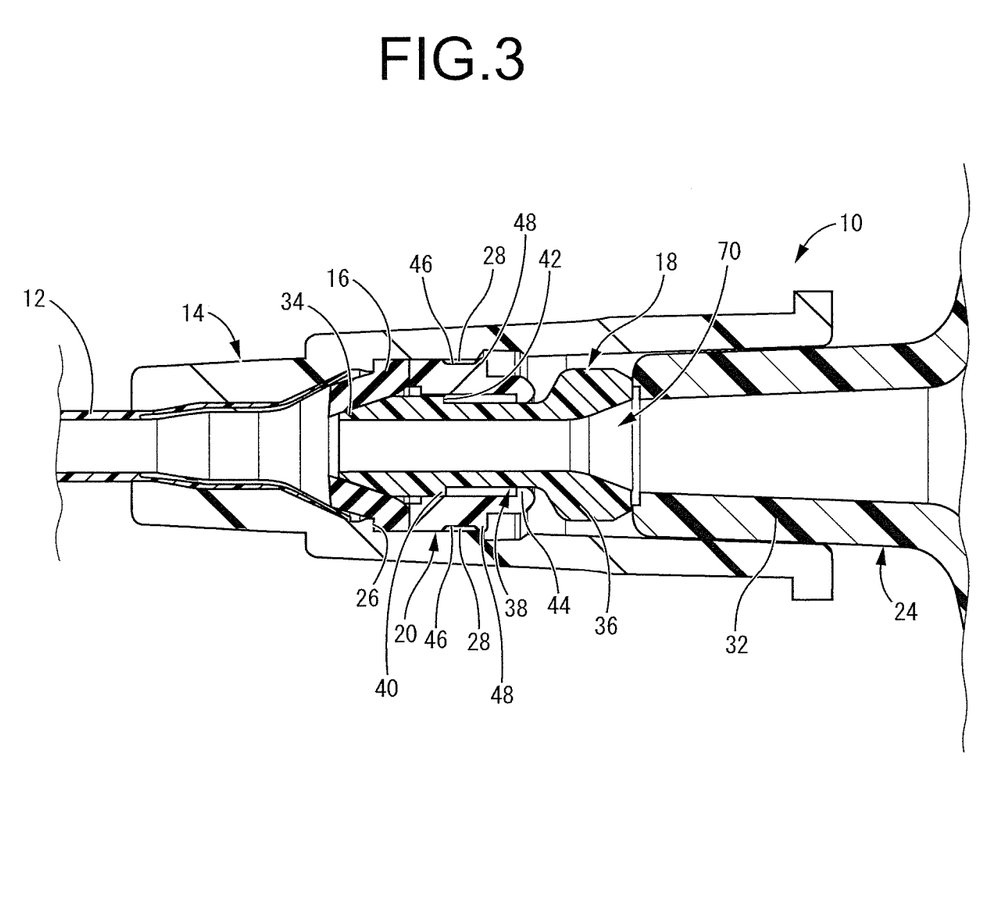
FIG. 3 is a cross sectional view showing the time of connection of a male connector of the indwelling catheter (conduction state) of the embodiment of FIG. 1.
Figure 4:
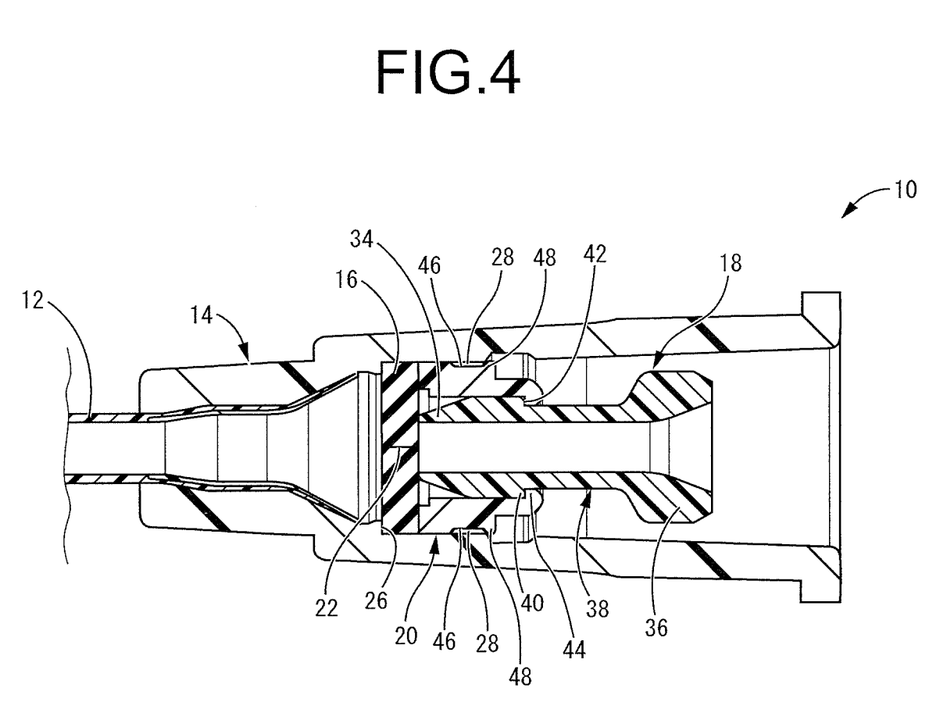
FIG. 4 is a cross sectional view showing the time of removal of the male connector of the indwelling catheter of the embodiment of FIG. 1.

Then, after the inner needle 30 has been pulled out, as shown in FIG. 3, the syringe 24 is inserted from the back end side exterior of the catheter base 14 and pushed in. Even in this state with the inner needle 30 pulled out, the slit 22 is quickly closed, and the hemostatic condition is maintained by the hemostasis valve 16. Also, when the syringe 24 is inserted from the back end side of the catheter base 14 and the pusher 18 is pushed toward the front by a tip 32 of the syringe 24, the tip of the pusher 18 pushed by the syringe 24 is pushed against the hemostasis valve 16. However, though the taper having tapered form is provided to the outer circumference surface, the tip of the pusher 18 is too thick to pass through the slit 22 of the hemostasis valve 16. Accordingly, the hemostasis valve 16 pushed by the pusher 18 is elastically deformed so as to bend and extend toward the front which is the pushing-in direction of the syringe 24 facing the center part of the slit 22 from the fixed outer circumference part, and the slit 22 is expanded to open. When the syringe 24 is removed, as shown in FIG. 4, by the elastically deformed hemostasis valve 16 recovering its original state, the slit 22 can be kept in a closed state.

Here, the outer diameter of the hemostasis valve 16 of this embodiment in a single article state before being incorporated in the catheter base 14 has a larger outer diameter than the inner diameter of the site at which the hemostasis valve 16 is incorporated in the catheter base 14. Thus, in the state in FIGS. 2 and 4 incorporated in the catheter base 14, an external force facing inward in the radial direction is applied by the catheter base 14 on the outer circumference surface of the hemostasis valve 16, and the entire hemostasis valve 16 is compressed to the inside. Also, a tip part 34 of the pusher 18 is a tapered shape for which the diameter is reduced facing the tip side.

Therefore, as shown in FIG. 3, when the pusher 18 is in the second position that pushes open the hemostasis valve 16, pressure by elastic force is applied strongly inward in the radial direction by the hemostasis valve 16 on the tapered surface of the tip part 34 of the pusher 18, and as a result of the axial direction component force according to the tilting angle of the tapered surface of the tip part 34 acting as a push-back force to push the pusher 18 backward, movement of the pusher 18 in the backward direction when the syringe 24 is removed is effectively generated. The shape of the hemostasis valve 16 is preferably a disk shape, and by setting its compression rate (at the catheter base 14, the ratio by which the rubber external diameter becomes smaller after being fit to the rubber external diameter as a base) to for example 5 to 10%, and more preferably to approximately 7%, it is possible to have the hemostasis valve 16 be even more excellent in terms of generating movement of the pusher 18 to the back when the syringe 24 is removed. In order to stably obtain a hemostatic effect by the hemostasis valve 16 as well as to make the movement force of the pusher 18 in the backward direction even greater when the syringe 24 is removed, it is preferable to make the compression rate of the hemostasis valve 16 large. On the other hand, if the compression rate of the hemostasis valve 16 is too large, attaching of the hemostasis valve 16 to the catheter base 14 becomes difficult, and there is the risk of needing the pushing force of the syringe 24 required for the pusher 18 to push open the slit of the hemostasis valve 16 to be bigger.

As the material of the hemostasis valve 16, with this embodiment, isoprene rubber (IR) is used, but the invention is not limited to this, and it is possible to use materials with rubber elasticity, for example silicone, natural rubber, butyl rubber, chloroprene rubber, urethane rubber, styrene-butadiene rubber, ethylene propylene rubber, acrylic rubber, fluoro-rubber, thermoplastic elastomer or the like. The material of the hemostasis valve 16 is not limited to the materials noted above, and the shape of the hemostasis valve 16 is also not limited to a disk shape. As the shape of the hemostasis valve 16, it is also possible to use a duckbill (the shape of the mouth of a platypus) shape, a roughly "U" shape, or a cylinder shape. Furthermore, the slit 22 can be formed in a straight line, or a straight line cross, or can be formed in straight lines, curved lines or the like extending in radial fashion. It can also be a dot shape rather than being long. That said, it is not absolutely necessary to provide a slit in the hemostasis valve in advance, and for example it is also possible to pass the inner needle 30 through the hemostasis valve without a slit being formed, and to use this through hole as a dot shaped slit.

The pusher 18 is a hollow roughly tube shape for which both the tip and back end open, and is installed further to the back than the hemostasis valve 16 inside the catheter base 14. The tip part 34 of the pusher 18 with this embodiment forms a tapered shape that reduces in diameter facing the tip side, and meanwhile, a back end part 36 has a tapered expanding part formed so as to be able to connect with the syringe 24. Also, the outer diameter of an axial direction center part 38 which is between the tip part 34 and the back end part 36 of the pusher 18 of this embodiment has a diameter slightly smaller than the maximum outer diameter of the taper of the tip part 34. With this arrangement, a step 40 is formed at the forward end part of the axial direction center part 38 of the pusher 18. Also, this step 40 forms a recess part 42 extending at a designated distance in the front-back direction along the entire circumference on this pusher 18, and on this recess part 42, there is fit in a projecting part 44 provided along the entire circumference at the back end of the pusher guide 20. In particular, with this embodiment, the depth of the recess part 42 and the projecting height of the projecting part 44 are roughly equal. Thus, the constitution is such that when the pusher 18 moves, the bottom surface of the recess part 42 and the inner circumference surface of the projecting part 44 slide.

The pusher 18 is acceptable as long as the tip part 34 has a tapered shape, and has a constitution for which it is possible for the back end part 36 to connect to the syringe 24, and does not absolutely have to have the step 40 or recess part 42 of the axial direction center part 38. Also, the pusher 18 is formed from a synthetic resin such as polypropylene, polycarbonate, polyethylene, ABS or the like, and the material is preferably a hard material that does not deform when connecting the syringe 24. Furthermore, the recess part 42 of the pusher 18 and the projecting part 44 of the pusher guide 20 do not have to respectively be provided along the entire circumference. For example, the recess part 42 and the projecting part 44 can also be provided on a portion of the circumference, at mutually corresponding positions.

The pusher guide 20 forms a tube shape overall and is installed between the pusher 18 and the inner wall of the catheter base 14 at a position with the front surface in contact with the back surface of the hemostasis valve 16. With this embodiment, the inner wall of the pusher guide 20 has a diameter for which sliding along the pusher 18 is possible, and the projecting part 44 projecting inward in the radial direction is formed on the back end part. This projecting part 44 is constituted such that when the pusher 18 is moved, the bottom surface of the recess part 42 formed on the axial direction center part 38 of the pusher 18 and the inner circumference surface of the projecting part 44 slide.

Also, at the first position for which the pusher 18 does not push open the slit 22 of the hemostasis valve 16, the projecting part 44 abuts the step 40 provided at the front end part of the axial direction center part 38 of the pusher 18. With this arrangement, the projecting part 44 of the pusher guide 20 inhibits further movement of the pusher 18 backward, and also, the pusher guide 20 is able to align the pusher 18 at the first position, so as to prevent the situation of the pusher 18 breaking away from the catheter base 14. Having said that, at this first position, it is also possible to have a slight gap between the front end of the pusher 18 and the hemostasis valve 16, or between the recess part 42 of the pusher 18 and the projecting part 44 of the pusher guide 20, allowing a slight backlash in the axial direction of the pusher 18.

Also, the pusher 18 and the pusher guide 20 do not absolutely have to slide, but it is preferable that the pusher guide 20 be constituted so as to slide along the pusher 18 when the pusher 18 moves. With this arrangement, it is possible for the pusher 18 to move straight without wobbling, and as a result, it is possible to more precisely and stably open and close the slit 22 of the hemostasis valve 16 properly. Also, when moving the pusher 18 to the back by the syringe 24 being removed as well, with the pusher guide 20, it is possible to move the pusher 18 to the first position without wobbling. By so doing, it is possible to prevent the situation of the pusher 18 being in a state tilted in relation to the axial direction of the catheter base 14 and the syringe 24 not being able to suitably connect to the catheter base 14, or a situation of the pusher 18 moving while tilted forward even when the syringe 24 is pressed forward, or the pusher 18 not moving forward.

Meanwhile, when the pusher 18 is positioned at the second position at which it pushes open the slit 22 of the hemostasis valve 16, the tip part 34 of the pusher 18 is positioned inside the opening of the slit 22. Then, the front end part of the pusher guide 20 and the tip part 34 of the pusher 18 are abutting, and the inner circumference surface of the projecting part 44 which is the back end part of the pusher guide 20 and the bottom surface of the recess part 42 are abutting. In this way, the pusher guide 20 presses the pusher 18 at two points, so it is possible to stably align the pusher 18 at the second position.

Also, on the outer circumference surface of the pusher guide 20 of this embodiment, a pusher guide fixing receiver 46 which can engage with the pusher guide fixing part 28 provided on the inner circumference surface of the catheter base 14 is provided at a corresponding position on the circumference, and the catheter base 14 and the pusher guide 20 are fixed by engaging of the concave and convex parts of the pusher guide fixing receiver 46 and the pusher guide fixing part 28. A convex part 48 projecting outward in the radial direction is provided further to the back from the pusher guide fixing receiver 46, and when the product is assembled, the hemostasis valve 16, the pusher 18, the pusher guide 20, and an inner needle assembly 50 are inserted inside the catheter base 14 in that order, and it is possible to assemble the product simply by pushing in. In this way, since it is possible to assemble simply, the product can be manufactured with good efficiency. Accordingly, it is possible to suppress costs for manufacturing, and to suppress costs themselves when providing to patients.

The shape of the pusher guide 20 is not limited to the shape in FIG. 1 to FIG. 4 which show this embodiment, and it is also acceptable as long as it is a constitution for which it is possible to restrict the position of the pusher 18 from the first position to the second position. Also, for the pusher guide fixing part 28 and the pusher guide fixing receiver 46, these are acceptable as long as they have a shape by which the catheter base 14 and the pusher guide 20 can be fixed to each other. For example, with this embodiment, these were provided at mutually corresponding positions on a part of the circumference, but it is also possible to provide them respectively along the entire circumference. Also, it is preferable that the material of the pusher guide 20 be a hard material, and by using a hard material, it is possible to more stably guide and straightly insert the pusher 18 into the hemostasis valve 16.

The inner needle assembly 50 includes the inner needle 30, an inner needle hub 52, and a protector 54. The inner needle 30 has a tube shape that is long with a small diameter, and though omitted from the illustration, the front end has a pointed shape. With this embodiment, the inner needle assembly 50 is inserted to be able to be inserted and removed freely in the tube 12 and the catheter base 14, and the front part of the inner needle 30 projects forward from the tube 12. Then, the back part of the inner needle 30 is formed as an integrated unit by being inserted inside the roughly tube shaped inner needle hub 52 made of synthetic resin. The protector 54 includes a needle tip exposure prevention member 56 that covers the tip of the inner needle 30 when removing the inner needle 30 from the indwelling catheter 10, a ring 58 that encloses the needle tip exposure prevention member 56, and a pressing part 60 that extends out further forward from the front end of the ring 58.

A conventional known item can be used for this needle tip exposure prevention member 56, and we can list as an example a needle tip protector (30) or the like of JP-A-2008-173206 (Patent Document 2). Therefore, here, we will omit a detailed description of the needle tip exposure prevention member 56, and will give a brief description hereafter.

The needle tip exposure prevention member 56 of this embodiment is roughly a tube shape made of metal, and has an insertion hole 62 which extends in the front-back direction and in which the inner needle is inserted. Here, on the tip side of the inner needle 30, an expanding part (not illustrated) is provided for which the diameter is slightly large at least at a part on the circumference. The insertion hole 62 is formed at a diameter for which at the front side this expanding part can be passed through, while at the back side, the expanding part cannot be passed through. As a result, when the inner needle 30 is removed from the indwelling catheter 10, when external force is applied in the pullout direction to the back on the inner needle hub 52 of the inner needle assembly 50, a state occurs in which the expanding part of the inner needle 30 catches on the back side of the insertion hole 62, and the tip of the inner needle 30 is covered by the needle tip exposure prevention member 56. Then, when further external force is applied in the pullout direction of the inner needle hub 52, the inner needle assembly 50 is removed from the indwelling catheter 10 with the inner needle 30 covered by the needle tip exposure prevention member 56. The insertion hole 62 can have the diameter be made smaller gradually as it goes from front to back or smaller in steps, and it is also possible to have a shape for which a projection that projects inward is provided at the back so it locks the expanding part.

Also, with this embodiment, the needle tip exposure prevention member 56 is covered by the tube shaped ring 58 along the entire circumference, and furthermore at the front end of the ring 58, the pressing part 60 is formed extending further out to the front on at least a part of the circumference. In particular, with this embodiment, as shown in FIG. 1, at two locations (the up and down direction in FIG. 1), a pair of pressing parts 60, 60 are formed. These ring 58 and pair of pressing parts 60, 60 are formed as an integral unit using a hard synthetic resin. Here, a step 64 is provided on the front inner surface of the inner needle hub 52, and the inner diameter in front of the step 64 is larger than the inner diameter at the back of the step 64. Then, the outer diameter of the ring 58 is roughly equal to the inner diameter in front of the step 64, and in FIG. 1 which shows the time of skin puncture by the inner needle 30, the back part of the ring 58 is fit onto the front of the inner needle hub 52, and the back end surface of the ring 58 is made to abut the step 64.

Furthermore, when assembling the product, the pair of pressing parts 60, 60 extend in the front-back direction while being positioned between the outer circumference side of the pusher 18 and the inner circumference side of the catheter base 14. With this arrangement, when assembling the product, it is possible to push the pusher guide 20 to the front side of the pusher 18 inside the catheter base 14. After assembling the product, in other words, after the pusher guide 20 is pushed to the front side of the pusher 18, the pair of pressing parts 60, 60 functions as a fixing part. Specifically, with this embodiment, locking convex parts 66, 66 projecting to the outer circumference side are provided on the respective tip outer circumference surfaces of the pair of pressing parts 60, 60, while a pair of locking recess parts 68, 68 are provided on the inner circumference surface of the catheter base 14 at corresponding positions to the locking convex parts 66, 66. When the inner needle assembly 50 is pushed inside the catheter base 14 to the point at which these locking convex parts 66, 66 reach the position of the locking recess parts 68, 68, the inner needle assembly 50 is fixed inside the catheter base 14 by the locking action of the locking recess and convex parts 68 and 66. Furthermore, when the inner needle 30 is removed, by external force being applied in the pullout direction of the inner needle hub 52 to the back, the lock of the respective locking recess and convex parts 68 and 66 is released, and the inner needle assembly 50, in other words the inner needle 30, is removed from inside the catheter base 14.

Next, we will describe the indwelling catheter 10 of the present invention following the sequence of its use. When performing a transfusion or blood collection or the like from a blood vessel such as a peripheral vein or the like or under the skin or the like at the back of the hand of the patient, first, the tip of the inner needle 30 and the tube 12 of the indwelling catheter 10 shown in FIG. 1 punctures the patient's blood vessel or the like. After the tip of the inner needle 30 and the tube 12 has punctured the patient's blood vessel or the like, the catheter base 14 or the like is fixed to the back of the hand of the patient using tape or the like. In this way, by the tip of the inner needle 30 and the tube 12 puncturing the patient's blood vessel or the like, the hollow inner needle 30, the inner hole of the tube 12, and also the tip part of the inner hole of the catheter base 14 connected with the tube 12 are in communication with the patient's blood vessel or the like.

Figure 2:
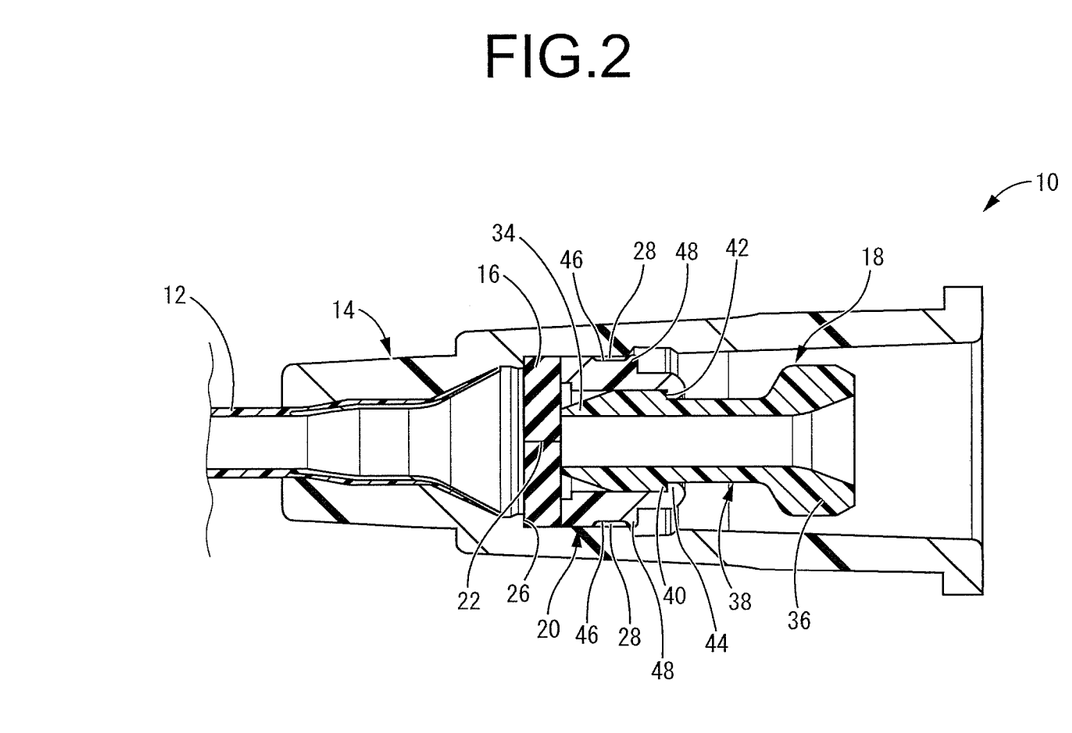
FIG. 2 is a cross sectional view showing the time of removal of the inner needle of the indwelling catheter (hemostatic condition) of the embodiment of FIG. 1.

After fixing of the catheter base 14 or the like using tape or the like to the back of the patient's hand is completed, as shown in FIG. 2, the inner needle 30 is removed from the catheter base 14. Specifically, as described previously, by external force in the pullout direction toward the back being applied on the inner needle hub 52 in which the back part of the inner needle 30 is inserted, the inner needle assembly 50, in other words the inner needle 30, is removed from inside the catheter base 14. Here, as soon as the inner needle 30 is removed, the slit 22 of the hemostasis valve 16 that was elastically deformed by the inner needle 30 recovers its original shape, and the slit 22 that is the opening and closing part of the hemostasis valve 16 closes. By so doing, the slit 22 which is the opening and closing part of the hemostasis valve 16 is closed simultaneous with removal of the inner needle 30, and it is possible to prevent blood leakage or the like from the indwelling catheter 10, for example, blood from the patient's blood vessel is prevented from flowing further back than the hemostasis valve 16 inside the catheter base 14. Also, when the inner needle 30 is removed, the inner needle 30 is covered by the needle tip exposure prevention member 56, so it is possible to prevent spraying of the blood adhered to the inner needle 30 to the surrounding area. In particular, since up to the tip of the inner needle 30 is covered by the needle tip exposure prevention member 56, it is possible to prevent accidental puncture of the worker.

After that, when starting the transfusion, blood collection or the like, as shown in FIG. 3, for example, the tip 32 of the syringe 24 illustrated as the male connector is inserted from the back part to inside the catheter base 14. Then, by doing taper joining of the tip 32 to the back side opening part of the catheter base 14 so as to be releasable, the tip 32 presses the pusher 18 forward. By so doing, the pusher 18 is moved forward while sliding on the inner wall of the pusher guide 20, and the tip part 34 of the pusher 18 presses the slit 22 of the hemostasis valve 16 so as to elastically deform it. Accordingly, the slit 22 which is the opening and closing part of the hemostasis valve 16 opens. This forms a fluid flow path 70 that starts from the patient blood vessel (not illustrated) and reaches the interior of the syringe 24 via the inner hole of the tube 12, the inner hole tip part of the catheter base 14, the slit 22 which is the opening and closing part of the hemostasis valve 16, the inner hole of the pusher 18, and the tip 32 of the syringe 24. Then, by pushing and pulling a plunger (not illustrated) of the syringe 24, the transfusion, blood collection or the like through the fluid flow path 70 is started.

During treatment, when temporary suspension of the operation of the transfusion, blood collection or the like is unavoidable, as shown in FIG. 4, the syringe 24 is removed from the catheter base 14, and by this removal, the pressing on the pusher 18 by the tip 32 of the syringe 24 is released. Accordingly, the elastic recovery force of the slit 22 of the hemostasis valve 16 which was being applied to the taper surface of the tip part 34 of the pusher 18 moves the pusher 18 to the back, and the pusher 18 moves automatically to the first position for which the slit 22 of the hemostasis valve 16 is not pushed open. As a result, the slit 22 of the hemostasis valve 16 recovers its original shape, and by the slit 22 which is the opening and closing part of the hemostasis valve 16 being reliably closed, in other words, by the fluid flow path 70 being reliably blocked at the hemostasis valve 16, it is possible to prevent blood leakage or the like from the indwelling catheter 10 during removal of the syringe 24.

When restarting the operation of the transfusion, blood collection or the like, the syringe 24 is again inserted from the back part to inside the catheter base 14, and in the same manner as noted above, the pusher 18 is pressed forward. By so doing, the slit 22 of the hemostasis valve 16 is pushed open, and the fluid flow path 70 that was in a blocked state by the hemostasis valve 16 is again in a communication state. At this time, because the pusher 18 is aligned by the pusher guide 20 in a state suitable for connection of the syringe 24, when the syringe 24 is connected again, it is possible to do the opening and closing operation of the slit 22 of the hemostasis valve 16 precisely without the occurrence of a situation in which the pusher 18 does not move, or a situation in which the slit 22 of the hemostasis valve 16 does not open properly. When the transfusion, blood collection or the like ends, by the syringe 24 being removed from the back part of the catheter base 14, in the same manner as noted above, the pusher 18 slides automatically to the back, and stops at the first position at which the slit 22 is not pushed open. Accordingly, the slit 22 which is the opening and closing part of the hemostasis valve 16 is closed, and the fluid flow path 70 is in a blocked state.

The indwelling catheter 10 with this kind of shape exhibits the following kinds of effects. Specifically, when the pusher 18 is in the first position at which it does not push open the slit 22 of the hemostasis valve 16, the fluid flow path 70 is in a blocked state by the hemostasis valve 16. Meanwhile, when the pusher 18 is in the second position at which it does push open the slit 22 of the hemostasis valve 16, the fluid flow path 70 is in a communication state starting from a blood vessel or the like and reaching the syringe 24 or the like. This kind of restriction of the pusher 18 at the first position or second position is alternatively selected by applying external force from the back to the back end part 36 of the pusher 18.

In other words, by the syringe 24 or the like being inserted from the back part to inside the catheter base 14, the pusher 18 moves to the second position and the fluid flow path 70 is in a communication state. On the other hand, by the syringe 24 or the like being removed from the catheter base 14, the pusher 18 moves to the first position and the fluid flow path 70 is in a blocked state. In this way, insertion and removal of the syringe 24 or the like works in conjunction with the fluid flow path 70 being in communication or blocked, and it is possible to easily perform restart or suspension of work such as transfusions, blood collections or the like over a plurality of times.

Also, with this embodiment, the structure is such that the recess part 42 of the pusher 18 abuts and slides against the projecting part 44 of the pusher guide 20, so it is possible to prevent the pusher 18 from tilting in relation to the catheter base 14. Furthermore, the projecting part 44 of the pusher guide 20 restricts the movement of the pusher 18 to the back, so it is not necessary to provide a special movement restriction means, and it is possible to inhibit the indwelling catheter 10 from becoming large.

Furthermore, with this embodiment, the hemostasis valve 16 is in a state always compressed to the inside by the catheter base 14. With this arrangement, when the syringe 24 or the like is removed, the elastic recovery force of the slit 22 of the hemostasis valve 16 is made larger, and for example it is not necessary to use biasing force of a coil spring as with the prior art. In other words, in comparison with the conventional catheter base, it is possible to make a diameter of the catheter base 14 smaller by the amount of the space in which the coil spring is installed. Thus, it is possible to promote making a more compact indwelling catheter 10.

Figure 5:
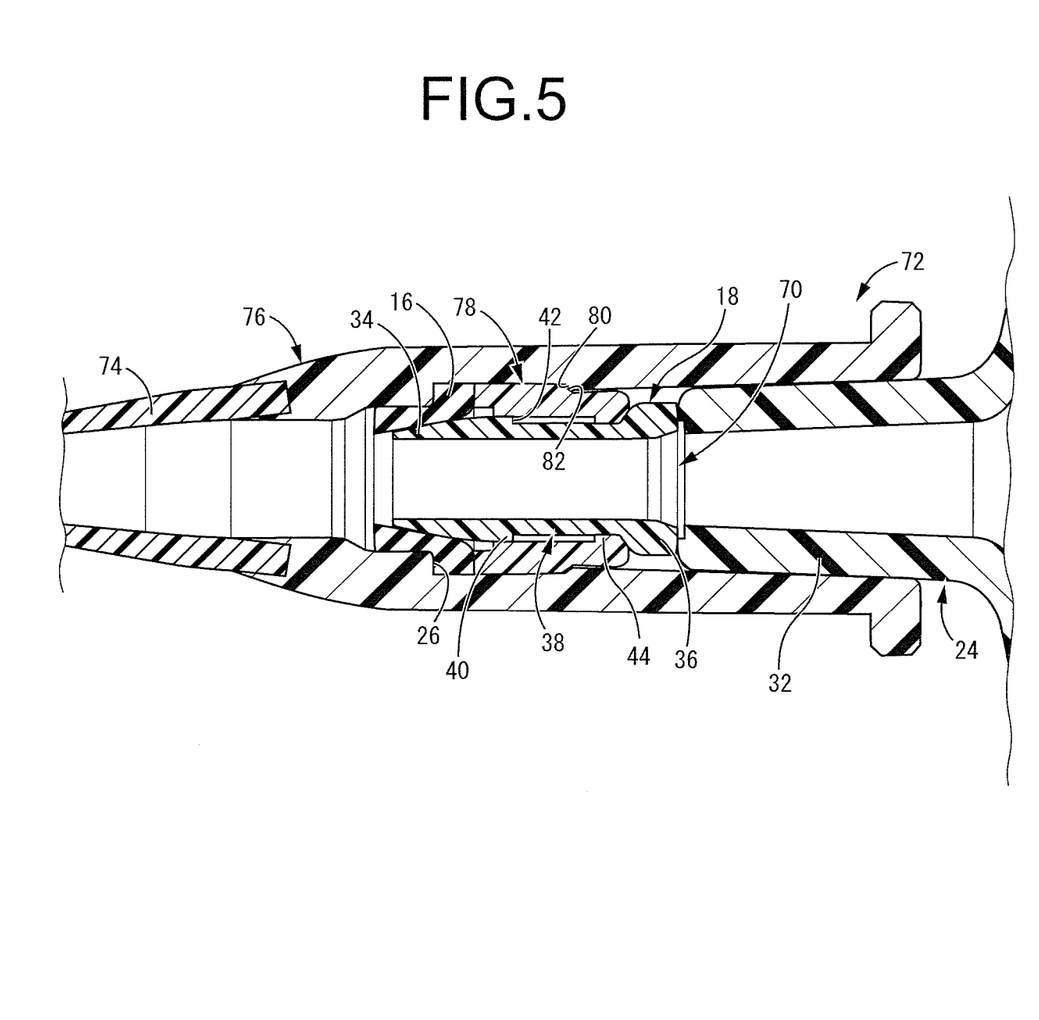
FIG. 5 is a cross sectional view showing the time of connection of a male connector of an indwelling catheter (conduction state) of another embodiment of the indwelling catheter according to the present invention.
Figure 6:
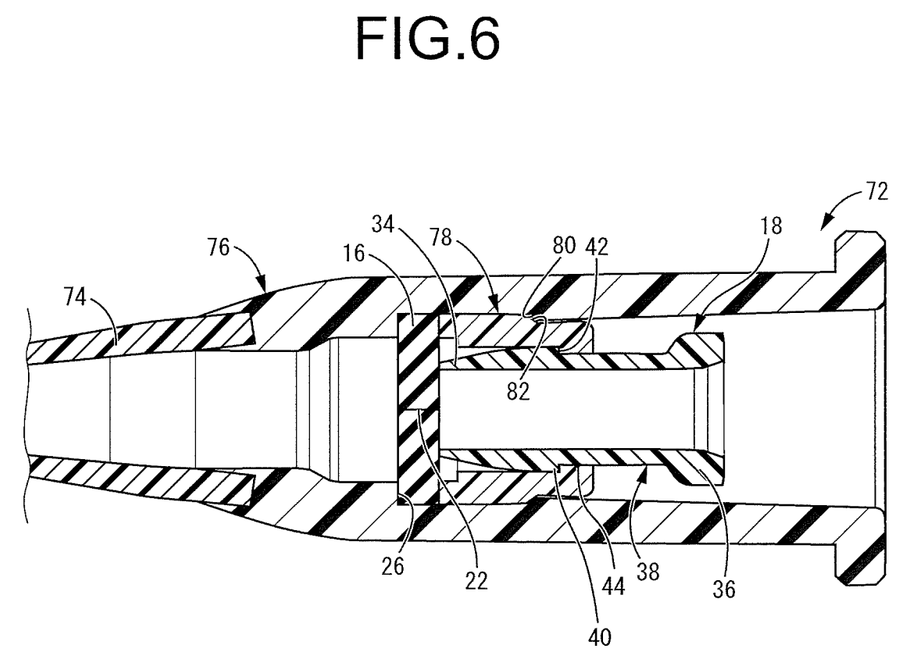
FIG. 6 is a cross sectional view showing the time of removal of the male connector of the indwelling catheter of the embodiment of FIG. 5.

Next, FIGS. 5 and 6 show an indwelling catheter 72 as another embodiment of the present invention. In the drawings of this embodiment, the same members and parts of the previously noted embodiment are given the same symbols, and a detailed description will be omitted. The structure of the indwelling catheter 72 of this embodiment is the same as that of the indwelling catheter 10 of the previously noted embodiment. Specifically, the indwelling catheter 72 has a tube 74 provided at the tip side thereof, a catheter base 76 provided at the back of the tube 74, the hemostasis valve 16 provided inside the catheter base 76, the pusher 18, a pusher guide 78 and the like. Here, in FIG. 5, the syringe 24 or the like is inserted from the back part exterior of the catheter base 76 of this embodiment, and the pusher 18 is moved to the second position. In FIG. 6, the syringe 24 or the like is removed from the back part of the catheter base 76, and the pusher 18 is moved to the first position.

With this embodiment, the main difference is the shape of the catheter base 76 and the pusher guide 78 compared to that of the catheter base 14 and the pusher guide 20 of the previously noted embodiment. Specifically, with the previously noted embodiment, while the pusher guide fixing part 28 is provided on the inner circumference surface of the catheter base 14, the pusher guide fixing receiver 46 is provided on the outer circumference surface of the pusher guide 20, and these components fix the pusher guide 20 to the inside of the catheter base 14. In contrast, with this embodiment, the inner circumference surface of the catheter base 76 has a tapered surface for which the diameter is reduced facing backward, and the outer circumference surface of the pusher guide 78 also has a tapered surface for which the diameter is reduced facing backward. Besides, compared to the compression rate of the outer circumference surface of the pusher guide 78, the compression rate of the inner circumference surface of the catheter base 76 is roughly the same or slightly larger, and the pusher guide 78 is fixed to the catheter base 76 by these tapered surfaces.

Therefore, with the previously noted embodiment, the pusher guide fixing part 28 and the pusher guide fixing receiver 46 were respectively made to be a convex shape and a concave shape, but a pusher guide fixing part 80 and a pusher guide fixing receiver 82 of this embodiment are both constituted with a tapered surface, and the pusher guide 78 is fixed to the catheter base 76 by the engagement action of these tapered surfaces. In this way, it will suffice for the pusher guide to restrict the pusher 18 to the first position and the second position, and for example, the shape or the like for the pusher guide to be fixed to the catheter base is not limited in any way. The indwelling catheter 72 with this kind of shape can exhibit the same effects as those of the previously noted embodiment.

Above, we described embodiments of the present invention, but the present invention is not to be interpreted as being limited to the specific notations of these embodiments, and it is possible to implement modes with various modifications, corrections, improvements or the like added based on the knowledge of a person skilled in the art.

For example, with the present invention, the needle tip exposure prevention member 56, the ring 58 enclosing the needle tip exposure prevention member 56, and the pressing part 60, in other words, the protector 54, is not absolutely necessary.

Also, the compression rate of the hemostasis valve 16 is not limited in any way, and can be suitably adjusted by the material or shape of the hemostasis valve 16. Also, it is acceptable to take into consideration the external force or the like added from the pusher 18.

Furthermore, with the previously noted embodiment, the inner circumference surface of the pusher guide 20 and the outer circumference surface of the pusher 18 overlap with a tube shaped surface extending at a designated length in the axial direction, whereby the pusher 18 was able to slide stably in the axial direction in relation to the pusher guide 20. In addition, the outer circumference surface of the pusher guide 20 and the inner circumference surface of the catheter base 14 overlap with a tube shaped surface extending at a designated length in the axial direction, whereby the pusher guide 20 is supported in a fixed state aligned with good precision by the catheter base 14. Then, as a result, the pusher 18 was able to move back and forth in the axial direction stably inside the catheter base 14. However, instead of this kind of overlapping structure using the tube shaped surface, for example, using a plurality of ring shaped abutting surfaces extending in the circumference direction parallel to and separated in the axial direction, it is also possible to have the inner circumference surface of the pusher guide 20 and the outer circumference surface of the pusher 18 or the outer circumference surface of the pusher guide 20 and the inner circumference surface of the catheter base 14 overlap, whereby it is possible to reduce the slide resistance of the pusher 18 in relation to the pusher guide 20 or the like while preventing backlash such as tilting at the overlapping part.

INDUSTRIAL APPLICABILITY

With the indwelling catheter of the present invention, though the structure is simple, it is possible to obtain an indwelling catheter that can be connected with a male connector a plurality of times, and furthermore, it is possible to obtain an indwelling catheter with excellent operability.

KEYS TO SYMBOLS

10, 72 Indwelling catheter
12, 74 Tube
14, 76 Cather base
16 Hemostasis valve
18 Pusher
20, 78 Pusher guide
24 Syringe
34 Tip part
44 Projecting part

The invention claimed is:
1. An indwelling catheter comprising:
a hollow catheter base having a tip and a back end, the back end being able to receive and connect a male connector configured to be inserted from a back end side exterior;
a tube provided at the tip of the catheter base;
a flexible hemostasis valve installed inside the catheter base;
a pusher installed at a back of the hemostasis valve; and
a pusher guide installed between the pusher and an inner wall of the catheter base;
wherein:
the pusher has a hollow constitution and a taper that decreases in diameter at a tip of the pusher;
the pusher guide is configured to restrict movement of the pusher between a first position in which the pusher does not push open the hemostasis valve, and a second position in which the pusher does push open the hemostasis valve and the taper of the pusher is positioned inside the hemostasis valve; and
a coil spring for moving the pusher is not provided within the catheter base.
2. The indwelling catheter according to claim 1, wherein the hemostasis valve is compressed inward in a radial direction by the catheter base.
3. The indwelling catheter according to claim 1, wherein the pusher guide forms a tube shape,
a projecting part projecting inward in a radial direction is provided on an inner wall of the pusher guide, and
movement of the pusher backward at the first position is restricted by the projecting part.
4. The indwelling catheter according to claim 1, wherein the hemostasis valve is configured to move the pusher from the second position to the first position by applying an elastic force against the taper of the tip of the pusher.

* * * * *